United States Patent [19]

Gallenkamp et al.

[11] Patent Number: 5,410,066

[45] Date of Patent: Apr. 25, 1995

[54] PROCESS FOR THE PREPARATION OF SUBSTITUTED PYRAZOLINES

[75] Inventors: Bernd Gallenkamp; Rainer Fuchs, both of Wuppertal, Germany

[73] Assignee: Bayer Aktiengesellschaft, Leverkusen, Germany

[21] Appl. No.: 279,123

[22] Filed: Jul. 22, 1994

Related U.S. Application Data

[60] Division of Ser. No. 169,936, Dec. 20, 1993, Pat. No. 5,380,868, which is a continuation of Ser. No. 984,785, Dec. 3, 1992, abandoned.

[30] Foreign Application Priority Data

Dec. 13, 1991 [DE] Germany .................. 41 14 187.0

[51] Int. Cl.⁶ .......................................... C07D 231/16
[52] U.S. Cl. ................... 548/375.1; 548/255; 548/267.2; 548/340.1; 548/561; 564/342; 564/343
[58] Field of Search .......... 548/375.1, 340.1; 564/342, 343

[56] References Cited

U.S. PATENT DOCUMENTS 5,070,098 12/1991 Fuchs et al. .

FOREIGN PATENT DOCUMENTS 0438690 7/1991 European Pat. Off. .

OTHER PUBLICATIONS

Synthetic Communications, Bd. 17, No. 7, 1987, Seiten 809–815 Takahashi et al.

Primary Examiner—Robert W. Ramsuer
Attorney, Agent, or Firm—Sprung Horn Kramer & Woods

[57] ABSTRACT

A new process for the preparation of pyrazolines of formula

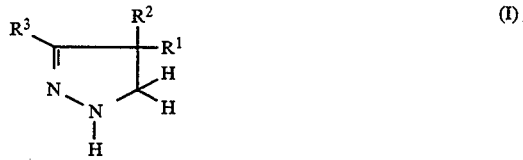

is provided, in which
$R^1$ and $R^3$ are identical or different and each represent optionally substituted aryl or optionally substituted and/or benzo-fused heterocyclyl with 5 or 6 ring members of which 1 to 4 are nitrogen atoms and the remainder are carbon atoms, and
$R^2$ represents hydrogen or alkyl, cycloalkyl or aryl, each of which is optionally substituted.

In this, in a first reaction stage, ketones of formula (II)

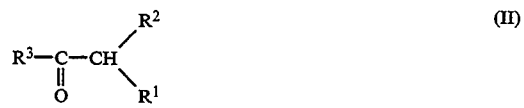

are reacted with bis-dialkylaminomethanes of formula (III)

$$(R^4)_2N-CH_2-N(R^4)_2 \qquad (III)$$

in which
$R^4$ represents alkyl,
optionally in the presence of a diluent, at temperatures between 0° C. and 100° C. and the substituted dialkylaminoalkyl ketones of general formula (IV)

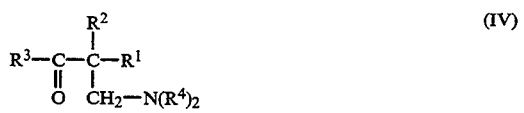

formed in this way are optionally isolated and in a second process stage are reacted with hydrazine (hydrate), optionally in the presence of a diluent, at temperatures between 0° C. and 100° C.

The compounds of formula (I) are known intermediates for the preparation of pyrazoline end products which have a powerful insecticidal action.

3 Claims, No Drawings

PROCESS FOR THE PREPARATION OF SUBSTITUTED PYRAZOLINES

This application is a divisional of application Ser. No. 08/169,936, filed Dec. 20, 1993, now U.S. Pat. No. 5,380,867, which is a continuation of application Ser. No. 07/984,785, filed Dec. 3, 1992, now abandoned.

The invention relates to a new process and new intermediates for the preparation of known substituted pyrazolines which may be used as intermediates for pesticides.

It is known that substituted pyrazolines are obtained when substituted alkenyl ketones are reacted with hydrazine (hydrate) (see EP-A 438690). However, in this process the substituted pyrazolines, and also the alkenyl ketones required as precursors, are obtained in only moderate yields. Moreover, the yields diminish with increasing batch size, so that corresponding large-scale industrial preparation is virtually impossible.

It has now been found that the substituted pyrazolines of general formula (I)

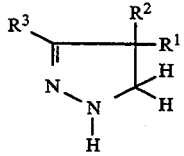
(I)

in which
R$^1$ and R$^3$ are identical or different and each represent optionally substituted aryl or optionally substituted and/or benzo-fused heterocyclyl with 5 or 6 ring members of which 1 to 4 are nitrogen atoms and the remainder are carbon atoms, and
R$^2$ represents hydrogen or alkyl, cycloalkyl or aryl, each of which is optionally substituted,
are obtained in very good yields and in very high quality if, in a first reaction stage, substituted ketones of general formula (II)

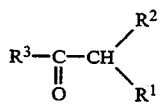
(II)

in which
R$^1$, R$^2$ and R$^3$ have the abovementioned meaning, are reacted with bis-dialkylaminomethanes of general formula (III)

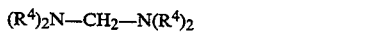
(III)

in which
R$^4$ represents alkyl,
optionally in the presence of a diluent, at temperatures between 0° C. and 100° C. and the substituted dialkylaminoalkyl ketones of general formula (IV)

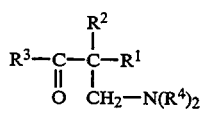
(IV)

in which

R$^1$, R$^2$, R$^3$ and R$^4$ have the abovementioned meaning formed in this way are optionally isolated and, in a second process stage, are reacted with hydrazine (hydrate), optionally in the presence of a diluent, at temperatures between 0° C. and 100° C.

Surprisingly, the substituted pyrazolines of formula (I) may be obtained in much higher yields and with better quality than in the known process according to EP-A 438690 by using the process according to the invention.

In contrast to the known process, the process according to the invention may be converted to an industrial scale without any problems. The process according to the invention therefore represents a valuable extension of the prior art.

For example, if α-(pyrazol-1-yl)-4-fluoroacetophenone and bis-dimethylamino-methane are used as starting materials, the course of the reaction during the process according to the invention may be outlined by the following reaction scheme:

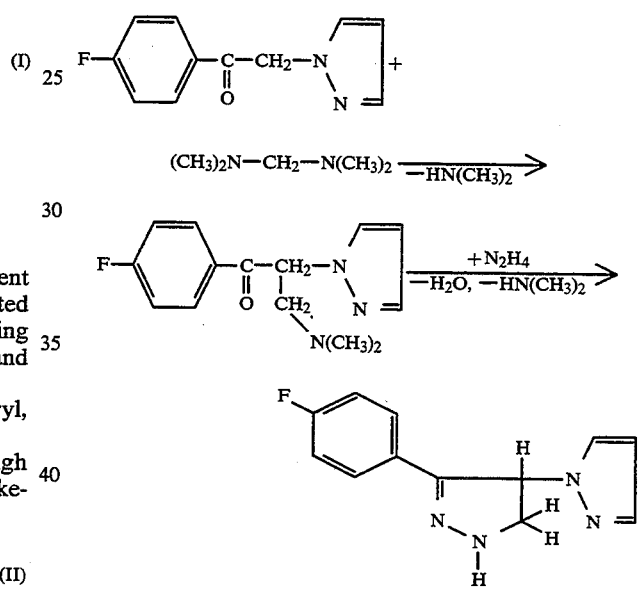

Preferred compounds of formula (I) prepared by the process according to the invention are those in which
R$^1$ and R$^3$ are identical or different and each represent phenyl or naphthyl, each of which is optionally substituted by halogen, cyano, nitro, C$_1$-C$_6$-alkyl, C$_1$-C$_6$-halogenoalkyl, C$_1$-C$_6$-alkoxy, C$_1$-C$_6$-halogenoalkoxy, C$_1$-C$_6$-alkylthio, C$_1$-C$_6$-halogenoalkylthio, C$_1$-C$_6$-alkylsulphinyl, C$_1$-C$_6$-halogenoalkylsulphinyl, C$_1$-C$_6$-alkylsulphonyl, C$_1$-C$_6$-halogenoalkylsulphonyl, di-(C$_1$-C$_4$-alkyl)-amino, C$_1$-C$_6$-alkoxy-carbonyl, C$_1$-C$_6$-halogenoalkoxycarbonyl, C$_1$-C$_2$-alkylenedioxy, C$_1$-C$_2$-halogenoalkylenedioxy, phenoxy (which is optionally substituted by halogen and/or C$_1$-C$_4$-halogenoalkyl) or phenylthio (which is optionally substituted by halogen and/or C$_1$-C$_4$ -halogenoalkyl), or each represent a pyrrole, pyrazole, imidazole, triazole, pyridine, pyridone, pyrimidine, pyrazine, pyridazine or triazine radical, each of which is optionally substituted by halogen, cyano, nitro, C$_1$-C$_6$-alkyl, C$_1$-C$_6$-halogenoalkyl, C$_1$-C$_6$-alkoxy, C$_1$-C$_6$-halogenoalkoxy, C$_1$-C$_6$-alkylthio, C$_1$-C$_6$-halogenoalkylthio, C$_1$-C$_6$-alkylsulphinyl, C$_1$-C$_6$- halogenoalkylsulphinyl, $C_1$–$C_6$-alkylsulphonyl or $C_1$–$C_6$-halogenoalkylsulphonyl, and $R^2$ represents hydrogen, $C_1$–$C_6$-alkyl optionally substituted by halogen, $C_3$–$C_6$-cycloalkyl optionally substituted by halogen and/or $C_1$–$C_4$-alkyl or phenyl optionally substituted by halogen or $C_1$–$C_6$-alkyl.

In particular, compounds of formula (I) prepared by the process according to the invention are those in which $R^1$ represents phenyl optionally substituted by halogen, cyano, nitro, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio, $C_1$–$C_2$-halogenoalkylthio, $C_1$–$C_4$-alkylsulphinyl, $C_1$–$C_2$-halogenoalkylsulphinyl, $C_1$–$C_4$-alkylsulphonyl, $C_1$–$C_2$-halogenoalkylsulphonyl, $C_1$–$C_2$-alkylenedioxy or $C_1$–$C_2$-halogenoalkylenedioxy, $R^2$ represents hydrogen, and $R^3$ represents a pyrazole or pyridone radical, each of which is bonded via nitrogen and is optionally substituted by halogen, cyano, nitro, $C_1$–$C_4$-alkyl, $C_1$–$C_2$-halogenoalkyl, $C_1$–$C_4$-alkoxy, $C_1$–$C_2$-halogenoalkoxy, $C_1$–$C_4$-alkylthio or $C_1$–$C_2$-halogenoalkylthio.

Halogen, in the definition of compounds of formula (I), preferably represents fluorine, chlorine, bromine or iodine.

Substituted dialkylaminoalkyl ketones of general formula (IV) as intermediates in the process according to the invention are not yet known from the literature and are also the subject of this patent application.

$R^1$, $R^2$ and $R^3$ in formula (IV), preferably or in particular, have those meanings which have already been stated above, in connection with the description of the compounds of formula (I) to be prepared according to the invention, as being preferable or particularly preferred for $R^1$, $R^2$ and $R^3$; $R^4$ preferably represents $C_1$–$C_6$-alkyl, in particular methyl, ethyl, propyl or butyl.

The substituted ketones to be used as starting materials for the preparation of compounds of formula (I) in the process according to the invention are defined in general terms by formula (II). $R^1$, $R^2$ and $R^3$ in formula (II) preferably or particularly have those meanings which have already been stated above as preferable or particularly preferred for $R^1$, $R^2$ and $R^3$ in connection with the description of the compounds of formula (I) to be prepared according to the invention.

Starting materials of formula (II) are known and/or may be prepared using methods known per se (see EP-A 438690).

The bis-dialkylaminomethanes also to be used as starting materials in the process according to the invention are defined in general terms by formula (III). In formula (III), $R^4$ preferably represents $C_1$–$C_6$-alkyl, in particular methyl, ethyl, propyl or butyl.

The starting materials of formula (III) are known organic synthetic chemicals.

The first stage of the process according to the invention, for obtaining the intermediates of formula (IV), may be performed either without the addition of a diluent or in the presence of a diluent. In this case, suitable diluents are in particular aliphatic, alicyclic or aromatic, optionally halogenated, hydrocarbons, such as, for example, pentane, hexane, heptane, cyclohexane, methylcyclohexane, benzene, toluene, xylene, methylene chloride, chloroform, tetrachloromethane, chlorobenzene and o-dichlorobenzene. The use of methylene chloride as a diluent is especially preferred in this case.

The reaction temperatures may be varied over a wide range when performing the first stage of the process according to the invention. The temperatures used may be between 0° C. and 100° C. preferably between 5° C. and 80° C., particular between 10° C. and 50° C.

To perform the first stage of the process according to the invention, in general between 0.9 and 1.5 mol, preferably between 1.0 and 1.2 mol, of bis-dialkylaminomethane of formula (III) are used per mole of substituted ketone of formula (II). The starting materials of formula (II) and (III), and preferably a diluent such as, for example, methylene chloride, are generally mixed at temperatures between about 5° C. and about 30° C. and then stirred until the end of the reaction, preferably at 30° C. to 100° C. The resulting intermediates of formula (IV) may in general be isolated in crystalline form, when the mixture is concentrated by evaporation under reduced pressure after the end of the reaction, the residue is stirred with a non-polar solvent, such as, for example, hexane, and the crystalline product is isolated by suction filtration. Preferably, the process for preparing compounds of formula (I) is performed without intermediate isolation of compounds (IV).

The second stage of the process according to the invention is preferably performed using a diluent. Virtually all inert organic solvents are suitable diluents. These preferably include aliphatic and aromatic, optionally halogenated, hydrocarbons such as pentane, hexane, heptane, cyclohexane, petroleum ether, petrol, ligroin, benzene, toluene, xylene, methylene chloride, ethylene chloride, chloroform, tetrachloromethane, chlorobenzene and o-dichlorobenzene, ethers such as diethyl and dibutyl ether, glycol dimethyl ether and diglycol dimethyl ether, tetrahydrofuran and dioxane, ketones such as acetone, methyl ethyl, methyl isopropyl and methyl isobutyl ketone, esters such as methyl acetate and ethyl acetate, nitriles such as, for example, acetonitrile and propionitrile, amides such as, for example, dimethylformamide, dimethylacetamide and N-methylpyrrolidone, as well as dimethyl sulphoxide, tetramethylene sulphone and hexamethylphosphoric triamide, and also alcohols such as methanol, ethanol, n- and iso-propanol, n-, iso-, sec- and tert-butanol. Ethanol is especially preferred as the solvent for the second stage of the process according to the invention.

The reaction temperatures may be varied over a wide range when performing the second stage of the process according to the invention. The temperatures used may be between 0° C. and 100° C., preferably between 0° C. and 60° C., in particular between 0° C. and 40° C.

To perform the second stage of the process according to the invention, in general between 0.9 and 1.5 mol, preferably between 1.0 and 1.2 mol, of hydrazine (hydrate) are used, relative to 1 mol of starting compound of formula (II).

In a first variant of the process, the intermediate of formula (IV), isolated as stated above, is taken up in a diluent, preferably ethanol. Hydrazine (hydrate) is then metered in slowly and the reaction mixture stirred for several hours. After cooling, the crystalline product can in general be isolated by suction filtration.

In a second variant of the process, hydrazine (hydrate) is added directly to the reaction mixture after performing the first stage of the process, i.e. intermediate isolation of the intermediate of formula (IV) is dispensed with. The mixture is stirred until the end of the reaction and worked up in the normal way (see the preparation examples).

In a third, especially preferred variant of the process, the first stage of the process is performed as stated above using methylene chloride as diluent. Then the mixture is concentrated by evaporation, the residue is taken up in, ethanol and hydrazine (hydrate) is added to it. The reaction mixture is then stirred until the end of the reaction. After cooling, the product may be isolated by suction filtration. However, it may also be advantageous to evaporate the mixture after the end of the reaction, to stir up the residue with another solvent, such as, for example, water, and then subject the mixture to suction filtration (see preparation examples).

The substituted pyrazolines of formula (I) to be prepared by the process according to the invention may be used as intermediates in the preparation of pesticides (see EP-A 438 690).

Conversion of a compound of formula (I) to an insecticidal end product may be elucidated using the following example:

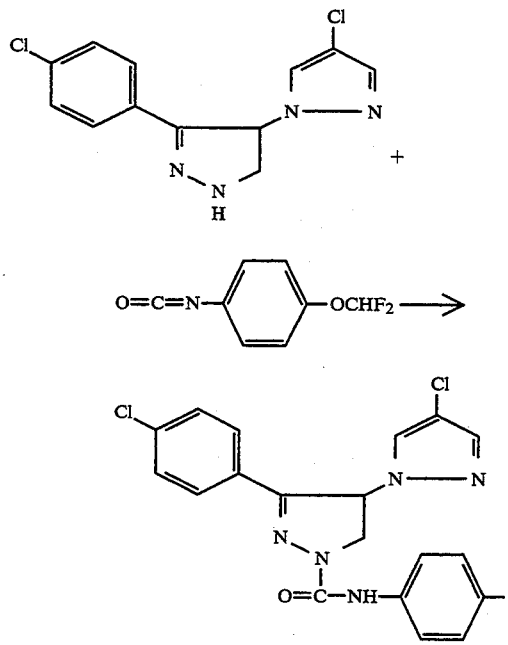

Compound in accordance with EP-A 438 690.

PREPARATION EXAMPLES

EXAMPLE 1

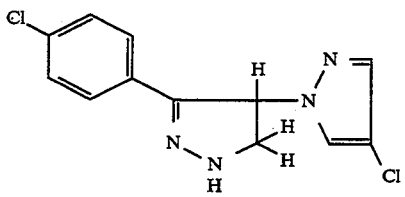

107 g (1.05 mol) of bis-dimethylaminomethane are added to a solution of 255 g (1.0 mol) of α-(4-chloro-pyrazol-1-yl)-4-chloro-acetophenone in 900 ml of dichloromethane at 20° C. to 25° C. The mixture is then heated under reflux for 90 minutes. After cooling to 20° C., 55 g (1.1 mol) of hydrazine hydrate are added dropwise over the course of 15 minutes. The reaction mixture is then stirred for 20 hours at 20° C. and finally for 30 minutes at 5° C. The crystalline product is isolated by suction filtration.

115 g (41% of theory) of 3-(4-chloro-phenyl)-4-(4-chloropyrazol-1-yl)-4,5-dihydro-1H-pyrazole with a melting point of 176° C. are obtained.

The filtrate is shaken, the organic phase is separated off, washed twice with 200 ml of water each time, dried with sodium sulphate and filtered. The filtrate is evaporated under a water pump vacuum and the residue is stirred up with diisopropyl ether. The crystalline product obtained in this way is isolated by suction filtration.

A further 47.2 g (17% of theory) of the abovementioned product is obtained in this way.

Overall yield: 162.2 g (58% of theory).

EXAMPLE 2

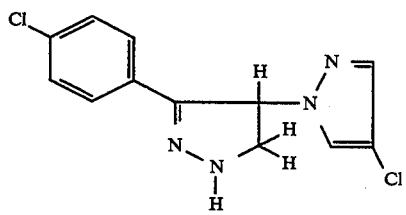

450 g (4.4 mol) of bis-dimethylaminomethane are added to a mixture of 1020 g (4.0 mol) of α-(4-chloro-pyrazol-1-yl)-4-chloro-acetophenone and 1600 ml of methylene chloride at 20° C. to 25° C. The reaction mixture is heated under reflux for 15 hours and then evaporated under a water pump vacuum. The remaining residue is taken up in 4 litres of ethanol and then 232 g (4.64 mol) of hydrazine hydrate are added to the mixture dropwise over the course of 15 minutes. After about 30 minutes a clear solution is produced and after approximately another 30 minutes the product begins to crystallise. The mixture is stirred for about 5 hours at 25° C. to 30° C. and then for about 30 minutes at 10° C.; the crystalline product is then isolated by suction filtration.

983 g (87% of theory) of 3-(4-chloro-phenyl)-4-(4-chloro- pyrazol-1-yl) -4,5-dihydro-1H-pyrazole with a melting point of 176° C. are obtained.

EXAMPLE 3

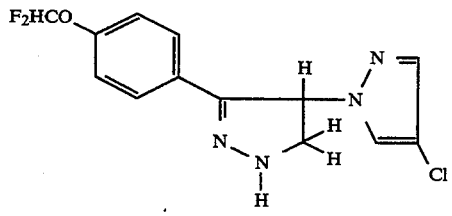

56.2 g (0.55 mol) of bis-dimethylaminomethane are added to a mixture of 143 g (0.5 mol) of α-(4-chloro-pyrazol-1-yl) -4-difluoromethoxy-acetophenone and 450 ml of methylene chloride at 20° C. The reaction mixture is heated under reflux for 19 hours and then evaporated under a water pump vacuum. The remaining residue is taken up in 750 ml of ethanol and treated with 27 g (0.54 mol) of hydrazine hydrate, whereupon the internal temperature rises from 25° C. to 35° C. The reaction mixture is stirred for another 5 hours and then evaporated under a water pump vacuum. The residue is stirred up with 1 liter of water and the crystalline product is isolated by suction filtration.

154 g (98% of theory) of 3-(4-difluoromethoxyphenyl)-4-(4-chloro-pyrazol-1-yl) -4,5-dihydro-1H-pyrazole with a melting point of 93° C. are obtained.

INTERMEDIATES OF FORMULA (IV)

EXAMPLE (IV-1)

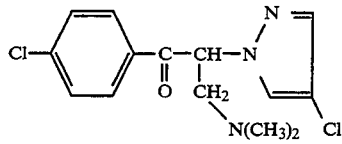

A mixture of 143 g (0.56 mol) of α-(4-chloro-pyrazol-1-yl)-4-chloro-acetophenone, 63 g (0.62 mol) of bis-dimethylaminomethane and 500 ml of methylene chloride is heated under reflux for 15 hours and then evaporated under a water pump vacuum. The residue is stirred up with 500 ml of hexane and the crystalline product is isolated by suction filtration.

148 g (85% of theory) of α-(4-chloropyrazol-1-yl)-α-dimethylaminomethyl-4-chloro-acetophenone with a melting point of 107° C. are obtained.

We claim:

1. A process for the preparation of a substituted dialkylaminomethyl ketone of the formula

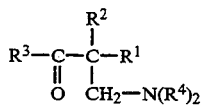

in which

R$^3$ is substituted phenyl, the substituents being selected from the group consisting of halogen, cyano, nitro, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, C$_1$–C$_6$-halogenoalkylthio, C$_1$–C$_6$-alkylsulphinyl, C$_1$–C$_6$-halogenoalkylsulphinyl, C$_1$–C$_6$-alkylsulphonyl, C$_1$–C$_6$-halogenoalkylsulphonyl,di-(C$_1$–C$_6$-alkyl)-amino, C$_1$–C$_6$-alkoxycarbonyl, C$_1$–C$_6$-halogenoalkoxygenocarbonyl, C$_1$–C$_2$-alkylenedioxy, C$_1$–C$_2$-halogenoalkylenedioxy, phenoxy (which is optionally substituted by halogen and/or C$_1$–C$_4$-halogenoalkyl) and phenylthio (which is optionally substituted by halogen and/or C$_1$–C$_4$-halogenoalkyl), R$^1$ is a pyrrole, pyrazole, imidazole or triazole radical, each of which is optionally substituted by halogen, cyano, nitro, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, C$_1$–C$_6$-halogenoalkylthio, C$_1$–C$_6$-alkylsulphinyl, C$_1$–C$_6$-halogenoalkylsulphinyl, C$_1$–C$_6$-alkylsulphonyl, and/or C$_1$–C$_6$-halogenoalkylsulphonyl, R$^2$ is hydrogen, C$_1$–C$_6$-alkyl optionally substituted by halogen, C$_3$–C$_6$-cycloalkyl optionally substituted by halogen and/or C$_1$–C$_4$-alkyl, or phenyl optionally substituted by halogen or C$_1$–C$_6$-alkyl, R$^3$ is substituted phenyl, the substituents being selected from the group consisting of halogen, cyano, nitro, C$_1$–C$_6$-alkyl, C$_1$–C$_6$-halogenoalkyl, C$_1$–C$_6$-alkoxy, C$_1$–C$_6$-halogenoalkoxy, C$_1$–C$_6$-alkylthio, C$_1$–C$_6$-halogenoalkylthio, C$_1$–C$_6$-alkylsulphinyl, C$_1$–C$_6$-halogenoalkylsulphinyl, C$_1$–C$_6$-alkylsulphonyl, C$_1$–C$_6$-halogenoalkylsulphonyl,di-(C$_1$–C$_6$-alkyl)-amino, C$_1$–C$_6$-alkoxycarbonyl, C$_1$–C$_6$-halogenoalkoxycarbonyl, C$_1$–C$_2$-alkylenedioxy, C$_1$–C$_2$-halogenoalkylenedioxy, phenoxy (which is optionally substituted by halogen and/or C$_1$–C$_4$-halogenoalkyl) and phenylthio (which is optionally substituted by halogen and/or C$_1$–C$_4$-halogenoalkyl), and R$^4$ is alkyl with 1 to 6 carbon atoms, which consists essentially of reacting a substituted ketone of the formula

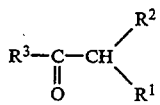

with a bis-dialkylamino methane of the formula

in a reaction medium consisting essentially of aliphatic, alicyclic or aromatic, optionally halogenated hydrocarbons, at a temperature between 0° and 100 ° C.

2. A process according to claim 1, in which

R$^1$ is a halogen-substituted pyrazole radical bonded via nitrogen,

R$^2$ is hydrogen, and R$^3$ is phenyl optionally substituted by halogen, cyano, nitro, C$_1$–C$_4$-alkyl, C$_1$–C$_2$-halogenoalkyl, C$_1$–C$_4$-alkoxy, C$_1$–C$_2$-halogenoalkoxy, C$_1$–C$_4$-alkylthio, C$_1$–C$_2$-halogenoalkylthio, C$_1$–C$_4$-alkylsulphinyl, C$_1$–C$_2$-halogenoalkylsulphinyl, C$_1$–C$_4$-alkylsulphonyl, C$_1$–C$_2$-halogenoalkylsulphonyl, C$_1$–C$_2$-alkylenedioxy, and/or C$_1$–C$_2$-halogenoalkylenedioxy.

3. A process according to claim 1, in which

R$^1$ is 4-chloropyrazol-1-yl,

R$^2$ is hydrogen,

R$^3$ is 4-chlorophenyl, and

R$^4$ is methyl.

* * * * *

UNITED STATES PATENT AND TRADEMARK OFFICE
CERTIFICATE OF CORRECTION

PATENT NO. : 5,410,066
DATED : April 25, 1995
INVENTOR(S) : Gallenkamp, et al.

It is certified that error appears in the above-indentified patent and that said Letters Patent is hereby corrected as shown below:

Title Page    [30] Foreign Application Priority Date: After
              " Dec. 13, 1991 [DE] Germany ... " delete
              " 41 14 187.0 " and substitute
              -- 41 41 187.0 --

Signed and Sealed this

Twenty-second Day of August, 1995

Attest:

BRUCE LEHMAN

*Attesting Officer*    *Commissioner of Patents and Trademarks*